United States Patent [19]

Colvin

[11] 4,431,849
[45] Feb. 14, 1984

[54] PROCESS FOR PREPARING A METHYL PHENOL

[75] Inventor: Howard A. Colvin, Akron, Ohio

[73] Assignee: The Goodyear Tire & Rubber Company, Akron, Ohio

[21] Appl. No.: 313,517

[22] Filed: Oct. 21, 1981

[51] Int. Cl.$^3$ .................. C07C 37/00; C07C 37/58
[52] U.S. Cl. .................. 568/799; 568/771; 568/772; 568/798; 568/802
[58] Field of Search .......... 568/799, 782, 772, 768, 568/798, 754, 802

[56] References Cited

U.S. PATENT DOCUMENTS

| | | | |
|---|---|---|---|
| 3,305,590 | 2/1967 | Pollitzer et al. | 568/798 |
| 3,437,699 | 4/1969 | Flickinger | 568/754 |
| 3,441,618 | 4/1969 | Flickinger | 568/754 |
| 3,646,235 | 2/1972 | Little et al. | 568/798 |
| 4,072,721 | 2/1978 | Strun et al. | 568/768 |
| 4,112,243 | 9/1978 | Nowak et al. | 568/768 |
| 4,163,863 | 8/1979 | Ikarashi et al. | 568/798 |

FOREIGN PATENT DOCUMENTS 2650416  5/1977  Fed. Rep. of Germany ...... 568/798

*Primary Examiner*—Werren B. Lone
*Attorney, Agent, or Firm*—D. O. Nickey; B. H. Hendricks

[57] ABSTRACT

A process for preparing a methyl phenol from a tertiary hydroperoxide in an oxidation product of an alkylbenzene of the general structural formula

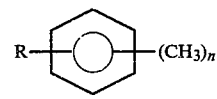

wherein R is a secondary alkyl group and n is an integer of 1 to 3, which comprises hydrogenating the oxidation product in the presence of a mineral acid medium with a hydrogenation catalyst.

16 Claims, No Drawings

PROCESS FOR PREPARING A METHYL PHENOL

TECHNICAL FIELD

This invention relates to a process for preparing a methyl phenol by rearranging a tertiary hydroperoxide in the presence of a primary hydroperoxide with a mineral acid and hydrogenating the primary hydroperoxide with a catalyst selected from the group comprising chromium, copper, palladium, platinum, nickel, ruthenium and rhodium in the rearrangement medium.

BACKGROUND OF THE INVENTION

Various methods of making methyl phenols are known in the art. One method consists of sulfonating toluene with sulfuric acid and fusing the sulfuric acid with sodium hydroxide at a high temperature to produce para-cresol and sodium sulfite as a by-product. Since toluene is a petroleum based raw material there is a strong incentive to find a less expensive method of producing a methyl phenol. Another drawback to the sulfonation process is the production of an inorganic by-product sodium sulfite which must be safely disposed of at an increased expense to the cost of production.

Another method of producing methyl phenol is known as the cymene process. This process consists of auto-oxidizing cymene to a tertiary hydroperoxide and rearranging the hydroperoxide to cresol and acetone. Unfortunately some of the methyl group is auto-oxidized and provides primary hydroperoxide. This has been found to decrease the overall selectivity to cresol. When the primary hydroperoxide is rearranged it produces formaldehyde and para-isopropyl phenol. The formaldehyde is found to condense with the cresol which further lowers the selectivity and complicates the isolation of the cresol. Thus it is apparent that before the primary hydroperoxide is rearranged it must be separated or destroyed.

One known method for removal of the primary hydroperoxide from the crude oxidate is by an extraction technique. This method comprises contacting the mixture of tertiary and primary hydroperoxide with an aqueous alkali metal hydroxide solution to form a caustic solution and then contacting the caustic solution with a water insoluble volatile organic solvent having a dielectric constant greater than 3 to form a solution of tertiary cymene hydroperoxide in the organic solvent and volatilizing the organic solvent to recover the tertiary cymene hydroperoxide. Using this method, it was found to be difficult to separate the hydroperoxides.

Another known method claims to selectively rearrange the tertiary hydroperoxide and thermally decompose the primary hydroperoxide. This method comprises subjecting a liquid oxidation product of cymene hydroperoxide to an acid catalyzed cleavage at a temperature of 60° to 90° C. until the concentration of cymene hydroperoxide in the liquid is 0.5 to 5 percent by weight. This solution is then neutralized with an alkali and thermally decomposing the hydroperoxide at a temperature of 100° to 250° C. This method creates an explosion hazard and the primary hydroperoxide is completely decomposed and cannot be recycled.

Still another known method claims to remove the primary hydroperoxide by converting it into starting material. This method comprises rearranging the hydroperoxide in the presence of mineral acid, neutralizing the rearrangeate and hydrogenating in a one or two step procedure. This presumably reduces the residual hydroperoxide to a benzyl alcohol. The benzyl alcohol is then converted into the parent alkylbenzene. A major disadvantage of this process is the requirement of the high temperatures during the hydrogenations.

An object of the present invention is to provide a process for preparing a methyl phenol at a low hydrogenation temperature resulting in a more economic process.

Another object of the present invention is to provide a process for preparing a methyl phenol in a manner which does not create an explosion hazard.

Another object of the present invention is to provide a process for preparing a methyl phenol of high purity with the added advantage of providing recycleable parent hydrocarbon.

A further object of the present invention is to provide a process for preparing a methyl phenol which minimizes or precludes inorganic by-products.

SUMMARY OF INVENTION

According to the present invention there is provided a process for preparing a methyl phenol from an alkyl benzene which comprises oxidizing an alkyl benzene having the general formula

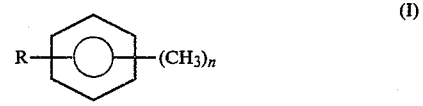

(I)

where R is a secondary alkyl group and n is an integer of 1 to 3, acid decomposing the oxidation product solution, hydrogenating the acid decomposition product in the presence of a hydrogenation catalyst with or without solvent and recovering the resulting methyl phenol of the general formula

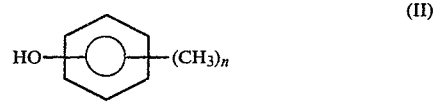

(II)

where n is an integer of from 1 to 3, from the hydrogenated solution.

DESCRIPTION OF THE PREFERRED EMBODIMENTS

Typical examples of the alkyl benzene include 3,5-dimethyl cumene, para-isobutyl toluene, 2,4,6-trimethyl cumene, 3,4-dimethyl cumene, 2,4-dimethyl cumene, ortho-cymene, meta-cymene and para-cymene, with para-cymene being preferred.

The alkyl benzene may be oxidized with air or molecular oxygen and the like according to the conventional oxidation method at atmospheric or higher pressures such as 1723.75 KPa.

The oxidation reaction of alkyl benzene may be carried out in the presence of or in the absence of oxidation catalysts represented from the group of water soluble metallo phthalocyanines, alkyl substituted phthalocyanines, polymer bound metal salts or quaternary ammonium halides.

The oxidation reaction temperature may range from about 80° to 200° C., preferably 90° to 115° C.

The oxidation product containing primary hydroperoxide and tertiary hydroperoxide is then acid decomposed with a solvent under conventional conditions in the presence of catalytic quantities of one or more mineral acids such as sulfuric, hydrochloric, perchloric and the like. The solvent is selected from one or more polar solvents such as methyl isobutyl ketone, acetone or 2-butanone.

The acid solution containing the decomposition product is hydrogenated in the presence of one or more hydrogenating catalysts.

The hydrogenating catalyst used in the hydrogenation reaction may be that used in the conventional hydrogenation reaction such as copper, chromium, ruthenium, rhodium, palladium, platinum, nickel or other metals having hydrogenation activities in composition thereof, with palladium being preferred. The hydrogenation catalyst may be unsupported or supported with carriers such as barium sulfate, asbestos, diatomaceous earth, alumina, activated carbon and silica, with activated carbon being preferred.

In the present invention, the pressure in the hydrogenation reaction is not critical and may range from about 0 to 689.5 kPa, with 310.275 KPa being preferred.

The temperature in the hydrogenation step is not critical and may range from about 0° to 200° C., with 25° to 50° C. being preferred.

The contact time of the hydrogenation catalyst will vary according to the particular catalyst selected. Preferred time is such that the hydrogenation is carried out until no more hydrogen uptake is observed.

After the hydrogenation step is completed, the reaction product can be neutralized by contacting with at least one base such as gaseous ammonia, ammonia hydroxide or an alkali hydroxide such as sodium hydroxide, potassium hydroxide or an alkali carbonate such as sodium carbonate and potassium carbonate, with gaseous ammonia being preferred.

After neutralization is completed the methyl phenol and the starting alkylbenzene are removed by distillation.

Typical examples of methyl phenols which are obtained by the process are 3,4-xylenol, 2,4,6-trimethyl phenol, 3,4-xylenol, 2,4-xylenol, ortho-cresol, meta-cresol and para-cresol.

The present invention can be carried out in a batch, semi-continuous and continuous process, preferably continuous.

Any reference to iodine number was determined by Method I as disclosed in Analytical Chemistry, Volume 36, No. 1, pages 194 and 195 (January 1964) incorporated herein.

All standards of measurement shall be expressed as parts by weight unless specified to the contrary.

The present invention will be described in more detail in the following examples. However, these examples are intended to illustrate the invention and are not to be construed to limit the scope of the invention.

EXAMPLE 1

Into a resin kettle equipped with an air powered stirrer, a reflux condenser topped with a gas inlet tube leading to a wet test meter, a thermometer and a sparge tube were placed 769 parts of para-cymene (which had been washed with sulfuric acid, 5 percent sodium hydroxide and water respectively), 15 parts of 75 percent solution of tertiary butyl peroxyisobutyrate and 101.6 parts of 2 percent sodium hydroxide. The mixture was heated to 95° C. with stirring as oxygen was bubbled in at 15 liters per hour. The pH of the aqueous phase was maintained between 9.5 and 10 by addition of 2 percent sodium hydroxide. After 14 hours of oxidation the iodine number of the organic phase was 22.7. The aqueous phase and the organic phase were separated and the aqueous phase was acidified to a pH of 1 with sulfuric acid and the solid filtered to yield para-isopropyl benzoic acid. The residual water was removed from the organic phase by azeotropic distillation at 9 torr. The dry oxidate (334 parts) was added in a thin stream to 0.4 part sulfuric acid in 276.8 parts of acetone at reflux. The reaction mixture was held at reflux for 13 minutes after addition was completed. The mixture was then cooled to room temperature with an ice bath. The reaction mixture was poured into a hydrogenation bottle which contained 4.5 grams of 5 percent palladium on carbon. The material was hydrogenated at 344.75 kPa of hydrogen at 45° C. for 45 minutes. The solutions were combined, neutralized with gaseous ammonia and filtered. The acetone was removed at atmospheric pressure by distillation.

The dark residue was vacuum distilled to yield 72 parts by weight of para-cresol and 614 parts by weight of para-cymene.

The remaining materials comprised 5 parts of para-isopropyl benzoic acid, 39 parts of acetone and 15 parts of residue.

The selectivity to para-cresol based on recovered para-cymene was 58 percent.

EXAMPLE 2

In a 300 cubic centimeter autoclave were charged 169 parts para-cymene (which had been washed with 2 percent sodium hydroxide), 6.0 parts of tertiary butyl hydroperoxide and 20.32 parts of 2 percent sodium hydroxide.

The reaction mixture was heated to 100° to 110° C. with stirring. The reactor was pressured to 1723.75 kPa with an oxygen-nitrogen mixture such that the percentage of oxygen in the head space did not exceed 4 percent. The aqueous phase was kept basic by periodic addition of 2 percent sodium hydroxide. The autoclave was set up so that the samples which were withdrawn for pH measurements could be returned. After 5 hours an iodine number of 26.2 was observed. The reactor was drained and the phases were separated. The aqueous phase was acidified with hydrochloric acid to pH 1 and para-isopropyl benzoic acid was filtered. The organic phase was azeotropically dried at reduced pressure. The total volume of oxidate (162.2 parts) was added to 0.235 part of sulfuric acid in 138.4 parts of acetone. The solution was refluxed for 23 minutes. The rearrangeate was immediately cooled in an ice bath to room temperature. The rearrangeate was poured into a Paar hydrogenation bottle which contained 2.8 parts of 5 percent palladium on carbon. The rearrangeate was hydrogenated for one hour at room temperature and 344.75 kPa of hydrogen. The hydrogenated solutions were combined and neutralized with gaseous ammonia. The solution was then filtered and the acetone was removed at atmospheric pressure by distillation. The organic phase was extracted with 264.46 parts of 6 percent potassium hydroxide. The aqueous phase was neutralized to pH 7 and extracted with ether. After drying with sodium sulfate the ether was evaporated and the residue was vacuum distilled to provide a para-cresol. The organic phase was vacuum distilled to provide para-cymene.

The yields on Example 2 were approximately 122.6 parts of para cymene, 18.8 parts of para-cresol, 0.8 part of para-isopropyl benzoic acid, 10.9 parts of acetone, 4.9 parts of residue from cymene distillation and 1.4 parts of residue from cresol distillation.

The selectivity to para-cresol based on recovered para-cymene was 49 percent.

EXAMPLE 3

In a 300 cubic centimeter autoclave were placed 168.5 parts of para-cymene (which had been washed with 2 percent sodium hydroxide), 6.0 parts of t-butyl hydroperoxide and 20.32 parts of 2 percent sodium hydroxide.

The reaction mixture was heated to 100° to 110° C. with stirring. The reactor was pressurized to 1723.75 kPa with an oxygen-nitrogen mixture such that the percentage of oxygen in the head space did not exceed 4 percent. The aqueous phase was kept basic by periodic addition of 2 percent sodium hydroxide. The autoclave was set up so that the samples which were withdrawn for pH measurements could be returned. After 5 hours an iodine number of 28.4 was observed. The reactor was drained and the phases were separated. The aqueous phase was acidified with hydrochloric acid to pH 1 and para-isopropyl benzoic acid was filtered. The organic phase was azeotropically dried at reduced pressure. The total volume of oxidate (167 parts) was added to 0.21 part of sulfuric acid in 138.4 parts of acetone. This solution was refluxed for 28 minutes. The rearrangeate was immediately cooled in an ice bath to room temperature. The rearrangeate was poured into a hydrogenation bottle which contained 2.8 grams of 5 percent palladium on carbon. The rearrangeate was hydrogenated for one hour at room temperature and 344.75 KPa of hydrogen. The hydrogenated solutions were combined and neutralized with gaseous ammonia. The solution was then filtered and the acetone was removed at atmospheric pressure by distillation. The organic phase was extraced with 264.43 parts of 6 percent potassium hydroxide. The aqueous phase was neutralized to pH 7 and extracted with ether. After drying with sodium sulfate the ether was evaporated and the residue was vacuum distilled to provide para-cresol. The organic phase was vacuum distilled to provide para-cymene.

The yields on Example 3 were approximately as follows: 119.3 parts of para-cymene, 18.1 parts of para-cresol, 5.1 parts of residue from cymene distillation, 1.5 parts of para-isopropyl benzoic acid, 1.8 parts of residue from cresol distillation and 9.7 parts of acetone.

The selectivity to para-cresol based on recovered para-cymene was 45 percent.

EXAMPLE 4

In a 300 cubic centimeter autoclave were placed 169 parts of para-cymene (which had been washed with 2 percent sodium hydroxide, 6.0 parts of t-butyl hydroperoxide and 20.32 parts of 2 percent sodium hydroxide.

The reaction mixture was heated to 100° to 110° C. with stirring. The reactor was pressured to 1723.75 kPa with an oxygen-nitrogen mixture such that the percentage of oxygen in the head space did not exceed 4 percent. The aqueous phase was kept basic by periodic addition of 2 percent sodium hydroxide. The autoclave was set up so that the samples which were withdrawn for pH measurements could be returned. After 5 hours an iodine number of 25.2 was observed. The reactor was drained and the phases were separated. The aqueous phase was acidified with hydrochloric acid to pH 1 and para-isopropyl benzoic acid was filtered. The organic phase was azeotropically dried at reduced pressure. The total volume of oxidate (162.2 parts) was added to 0.20 part of sulfuric acid in 134.45 parts of acetone. The solution was refluxed for 30 minutes. The rearrangeate was immediately cooled in an ice bath to room temperature. The rearrangeate was poured into a hydrogenation bottle which contained 2.8 grams of 5 percent palladium on carbon. The rearrangeate was hydrogenated for one hour at room temperature and 344.75 kPa of hydrogen. The hydrogenated solutions were combined and neutralized with gaseous ammonia. The solution was then filtered and the acetone was removed at atmospheric pressure by distillation. The organic phase was extracted with 264.46 parts of 6 percent potassium hydroxide. The aqueous phase was neutralized to pH 7 and extracted with ether. After drying with sodium sulfate the ether was evaporated and the residue was vacuum distilled to provide para-cresol. The organic phase was vacuum distilled to provide para-cymene.

The yields on Example 4 were approximately as follows: 129.6 parts of para-cymene, 17.2 parts para-cresol, 3.5 parts of residue from cymene distillation, 1 part of para-isopropyl benzoic acid, 1.8 part of residue from cresol distillation and 9.2 parts acetone.

The selectivity to para-cresol based on recovered para-cymene was 54 percent.

The results shown in Table I are those obtained in determining the purity of the para-cresol and recycleable starting material (para-cymene).

TABLE I

| Recycle Number | Recycle Cymene Purity | Cresol Purity |
| --- | --- | --- |
| 0 | 95.9% | — |
| 1 | 95.2 | 98% |
| 2 | 94.8 | 95 |
| 3 | 94.1 | 94 |
| 4 | 94.5 | 97 |

While certain representative embodiments and details have been shown for the purpose of illustrating the invention it will be apparent to those skilled in this art that various changes and modifications may be made therein without departing from the spirit or scope of the invention.

I claim:

1. A process for preparing a methyl phenol from an alkylbenzene having the general structural formula

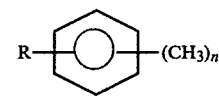

(I)

wherein R is a secondary alkyl group having from 3 to 4 carbon atoms and n is an integer from 1 to 3, inclusive, which comprises
  (A) contacting said alkylbenzene with molecular oxygen to provide an oxidation product solution containing tertiary hydroperoxide and primary hydroperoxide;
  (B) acid decomposing the hydroperoxide in the presence of catalytic quantities of a mineral acid catalyst;

(C) hydrogenating the acid decomposition product at a temperature ranging from about 0° to about 200° C. under a pressure of 0 to about 552 kPa for 0.2 to about 10 hours in the presence of a hydrogenation catalyst selected from the group comprising chromium, copper, palladium, platinum, nickel, ruthenium and rhodium;

(D) neutralizing the hydrogenation product with at least one base selected from the group comprising ammonia, ammonia hydroxide, alkali metal hydroxide or alkali metal carbonate; and (E) recovering from the hydrogenation product methyl phenol of the general structural formula

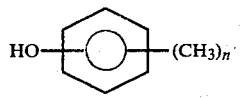
(II)

where n is as set forth above.

2. The process of claim 1 in which the alkylbenzene is para-cymene.

3. The process of claim 1 in which the methyl phenol is para-cresol.

4. The process of claim 1 in which the temperature at the hydrogenation step is from about 25° to about 45° C.

5. The process of claim 1 in which the base is gaseous ammonia.

6. The process of claim 1 in which the pressure of the hydrogenation step is 310.275 kPa.

7. The process of claim 1 in which the time of the hydrogenation reaction is from about 45 minutes to about one hour.

8. The process of claim 1 in which the oxidation reaction is at atmospheric pressure.

9. The process of claim 1 in which the oxidation reaction is at a pressure of 1723.75 kPa.

10. The process of claim 1 in which the hydrogenation catalyst is on a support.

11. The process of claim 1 in which the hydrogenation catalyst is palladium on carbon support.

12. The process of claim 1 in which the process is contiuous.

13. The process of claim 1 in which the process is semi-continuous.

14. The process of claim 1 in which the mineral acid catalyst is selected from the group comprising sulfuric acid, hydrochloric acid and perchloric acid or mixtures thereof.

15. The process of claim 14 in which the mineral acid catalyst is sulfuric acid.

16. The process of claim 14 in which the mineral acid catalyst is hydrochloric acid.

* * * * *